United States Patent [19]

Goldmann et al.

[11] Patent Number: 5,200,420

[45] Date of Patent: Apr. 6, 1993

[54] 2,6-DIALKYL-4-(BENZOTHIAZOL- OR BENZOXAZOL-4-YL-1,4-DIHYDROPYRIDINES

[75] Inventors: Siegfried Goldmann, Wuppertal; Horst Böshagen; Jürgen Stoltefuss, both of Haan; Alexander Straub; Rainer Gross, both of Wuppertal; Joachim Hütter, Leverkusen; Siegbert Hebisch; Martin Bechem, both of Wuppertal, all of Fed. Rep. of Germany

[73] Assignee: Bayer Aktiengesellschaft, Leverkusen, Fed. Rep. of Germany

[21] Appl. No.: 677,731

[22] Filed: Mar. 29, 1991

[30] Foreign Application Priority Data

Apr. 6, 1990 [DE] Fed. Rep. of Germany ....... 4011106

[51] Int. Cl.⁵ .................. C07D 413/04; A61K 31/44
[52] U.S. Cl. .................. 514/338; 514/302; 514/333; 546/270; 546/256; 546/116
[58] Field of Search .......... 546/270; 514/338

[56] References Cited

U.S. PATENT DOCUMENTS

| 4,380,547 | 7/1983 | Materne | 546/278 |
| 4,766,213 | 8/1988 | Juraszyk et al. | 546/270 |
| 4,849,433 | 7/1989 | Wehinger et al. | 546/270 |

FOREIGN PATENT DOCUMENTS

0080220 6/1983 European Pat. Off.
0217530 4/1987 European Pat. Off.

OTHER PUBLICATIONS

Ring Index, p. 152, No. 1152.

*Primary Examiner*—Jane T. Fan

[57] ABSTRACT

2,6-dialkyl-4-(benzothiazol- or benzoxazol-7-yl)-1,4-dihydropyridines which exhibit positive inotropic action with largely neutral vascular behavior, of the formula

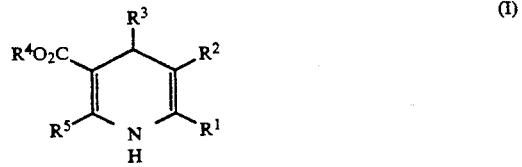
(I)

in which
$R^1$ and $R^5$ are identical or different and represent straight-chain or branched alkyl having up to 8 carbon atoms,
$R^2$ represents nitro or cyano, or
$R^1$ and $R^2$ together form a lactone ring of the formula

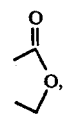

$R^3$ represents a radical of the formula

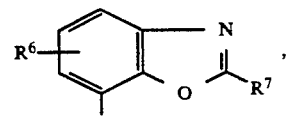

,

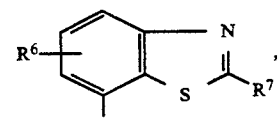

,

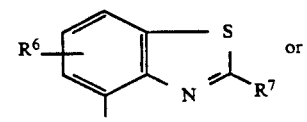 or

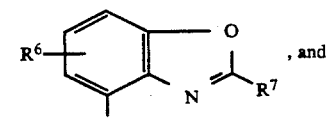

, and $R^4$–$R^7$ are defined hereinafter
and physiologically acceptable salts thereof.

11 Claims, No Drawings

2,6-DIALKYL-4-(BENZOTHIAZOL- OR BENZOXAZOL-4-YL-1,4-DIHYDROPYRIDINES

The invention relates to novel dihydropyridines substituted by heterocycles, processes for their preparation and their use in medicaments, in particular in agents having positive inotropic action.

It is already known that 1,4-dihydropyridines have vasodilating properties and can be used as coronary agents and antihypertensives [compare Brit. Patent 1,173,062 and 1,358,951; DE-OS (German Published Specification) 2,629,892 and 2,752,820]. Furthermore, it is known that 1,4-dihydropyridines cause an inhibition of the contractility of smooth and cardiac muscles and can be employed for the treatment of coronary and vascular disorders [compare Fleckenstein, Ann. Rev. Pharmacol. Toxicol., 17, 149–166 (1977)].

It is moreover known that, in addition to a positive inotropic cardiac action, 3-nitro-dihydropyridines can in general have the disadvantage of an undesired constricting action on the coronary vessels [compare Schramm et al., Nature 303, 535–537 (1983) and DE-OS (German Published Specification) 3,447,169].

With knowledge of the prior art, it was unforeseeable that the compounds according to the invention would have a positive inotropic action on the heart muscle, increasing the contractility and having largely neutral vascular behavior.

The invention relates to new dihydropyridines substituted by heterocycles, of the general formula (I)

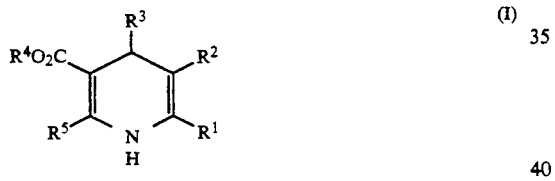

in which
R$^1$ and R$^5$ are identical or different and represent straight-chain or branched alkyl having up to 8 carbon atoms,
R$^2$ represents nitro or cyano, or
R$^1$ and R$^2$ together form a lactone ring of the formula

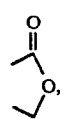

R$^3$ represents a radical of the formula

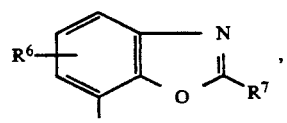

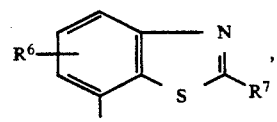

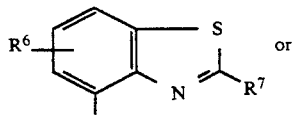

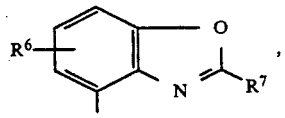

in which
R$^6$ denotes hydrogen, halogen or straight-chain or branched alkyl or alkoxy in each case having up to 8 carbon atoms, and
R$^7$ denotes aryl having 6 to 10 carbon atoms, which is optionally monosubstituted or disubstituted by identical or different substituents from the series comprising halogen, nitro, cyano, trifluoromethyl, trifluoromethoxy, trifluoromethylthio, straight-chain or branched alkyl, alkoxy or alkoxycarbonyl in each case having up to 8 carbon atoms, and carboxyl, or
denotes thienyl or pyridyl,
R$^4$ represents hydrogen, or
represents straight-chain or branched alkyl, alkenyl, alkadienyl or alkynyl in each case having up to 10 carbon atoms which are optionally monosubstituted or disubstituted by identical or different substituents from the series comprising halogen, hydroxyl, carboxyl, cyano, nitro, phenoxy and straight-chain or branched alkylthio, alkoxy, alkoxycarbonyl, acyl or acyloxy in each case having up to 8 carbon atoms, and phenoxy or phenyl, it being possible for the latter in turn to be monosubstituted or disubstituted by identical or different substituents from the series comprising halogen and straight-chain or branched alkyl or alkoxy in each case having up to 6 carbon atoms,
and their physiologically acceptable salts.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention exist in stereoisomeric forms which either behave as image and mirror image (enantiomers) or which do not behave as image and mirror image (diastereomers). The invention relates both to the antipodes and the racemic forms as well as the diastereomer mixtures. The racemic forms, like the diastereomers, can be separated into the stereoisomerically uniform components in a known manner (compare E. L. Eliel, Stereochemistry of Carbon Compounds, McGraw Hill, 1962).

Preferred compounds of the general formula (I) are those
in which $R^1$ and $R^5$ are identical or different and represent straight-chain or branched alkyl having up to 6 carbon atoms, $R^2$ represents nitro or cyano, or $R^1$ and $R^2$ together form a lactone ring of the formula

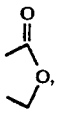

$R^3$ represents a radical of the formula

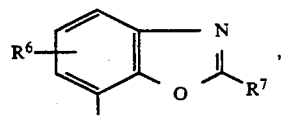

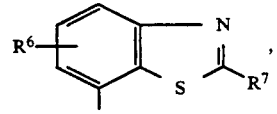

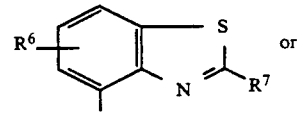

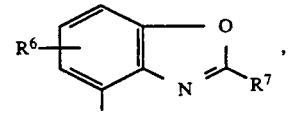

in which $R^6$ denotes hydrogen, fluorine, chlorine or straight-chain or branched alkyl or alkoxy in each case having up to 2 carbon atoms, and $R^7$ denotes phenyl which is optionally substituted by fluorine, chlorine, nitro, cyano, trifluoromethyl or by straight-chain or branched alkyl or alkoxy in each case having up to 6 carbon atoms, or denotes pyridyl or thienyl, $R^4$ represents hydrogen or represents straight-chain or branched alkyl or alkenyl in each case having up to 8 carbon atoms which are optionally substituted by fluorine, chlorine, hydroxyl, carboxyl, cyano, nitro or by straight-chain or branched alkylthio, alkoxy, alkoxycarbonyl, acyl or acyloxy in each case having up to 6 carbon atoms or by phenoxy or phenyl, and their physiologically acceptable salts.

Particularly preferred compounds of the general formula (I) are those in which $R^1$ and $R^5$ are identical or different and represent straight-chain or branched alkyl having up to 4 carbon atoms, $R^2$ represents nitro or cyano, or $R^1$ and $R^2$ together form a lactone ring of the formula

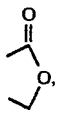

$R^3$ represents a radical of the formula

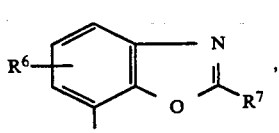

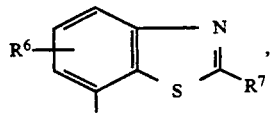

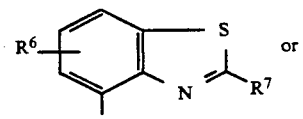

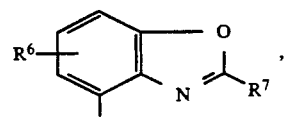

in which $R^6$ denotes hydrogen, chlorine or methyl, $R^7$ denotes phenyl which is optionally substituted by fluorine, chlorine, nitro, trifluoromethyl or straight-chain or branched alkyl, acyl or alkoxy in each case having up to 4 carbon atoms, or denotes pyridyl $R^4$ represents hydrogen, or represents straight-chain or branched alkyl having up to 6 carbon atoms, which is optionally substituted by hydroxyl, carboxyl, cyano or by straight-chain or branched alkoxycarbonyl, alkoxy or acyloxy in each case having up to 4 carbon atoms, and their physiologically acceptable salts.

A process for the preparation of the compounds of the general formula (I) according to the invention has additionally been found, characterized in that in the case in which $R^1$ and $R^2$ have the abovementioned meanings, but do not together form a lactone ring,

[A] compounds of the general formula (II)

$$R^3-CHO \qquad (II)$$

in which $R^3$ has the abovementioned meaning, are first reacted with acetoacetic esters of the general formula (III)

$$R^5-CO-CH_2-CO_2-R^4 \qquad (III)$$

in which $R^4$ and $R^5$ have the abovementioned meanings, if desired with the isolation of the corresponding ylidene compounds of the general formula (IV)

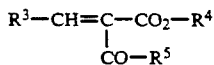 (IV)

in which
R³, R⁴ and R⁵ have the abovementioned meanings,
and then are reacted either with compounds of the formula (V)

R¹—CO—CH₂—R² (V)

in which
R¹ and R² have the abovementioned meanings,
in inert solvents, in the presence of ammonia or ammonium salts,
or directly with enamino derivatives of the general formula (VI)

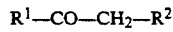 (VI)

in which
R¹ and R² have the abovementioned meanings,
or
[B] the aldehydes of the general formula (II) are first reacted with the compounds of the general formula (V), if desired with the isolation of the ylidene compounds of the general formula (VII)

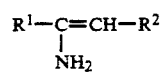 (VII)

in which
R¹, R² and R³ have the abovementioned meanings,
and in a next step reacted with the abovementioned compounds of the general formula (III) in inert solvents, in the presence of ammonia or ammonium salts or directly with enaminocarboxylic acid derivatives of the general formula (VIII)

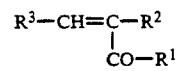 (VIII)

in which
R⁴ and R⁵ have the abovementioned meanings,
or in the case in which R¹ and R² together form a lactone ring,
[C] first, according to those methods given under [A] and [B], compounds of the general formula (Ia)

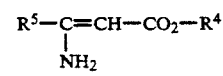 (Ia)

in which
R³, R⁴ and R⁵ have the abovementioned meanings,
R⁸ represents a C₁–C₆-alkyl radical and
R⁹ represents a leaving group such as, for example, chlorine or acetoxy, are prepared and, according to known methods, an acid- or base-catalyzed ring closure is added, and in the case in which R⁴ does not denote hydrogen,

[D] compounds of the general formula (I), in which R¹, R², R³, R⁴ and R⁵ have the abovementioned meanings and R⁴ represents hydrogen, are reacted with the corresponding alcohols, if appropriate via a reactive acid derivative, in which case by use of the enantiomerically pure carboxylic acid the corresponding enantiomers of the ester are obtained.

The processes according to the invention can be illustrated by the following equation:

[A]

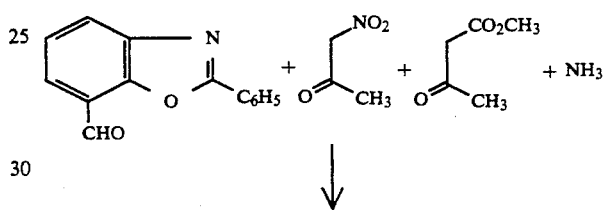

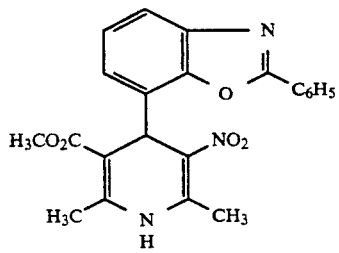

[A]

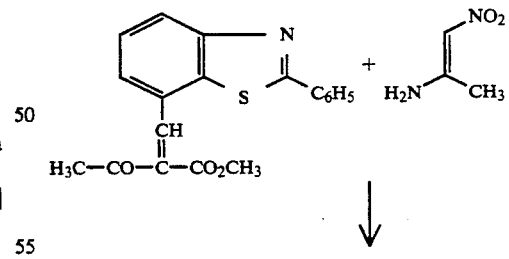

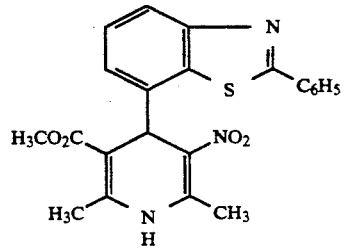

[B]

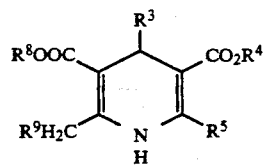

[C]

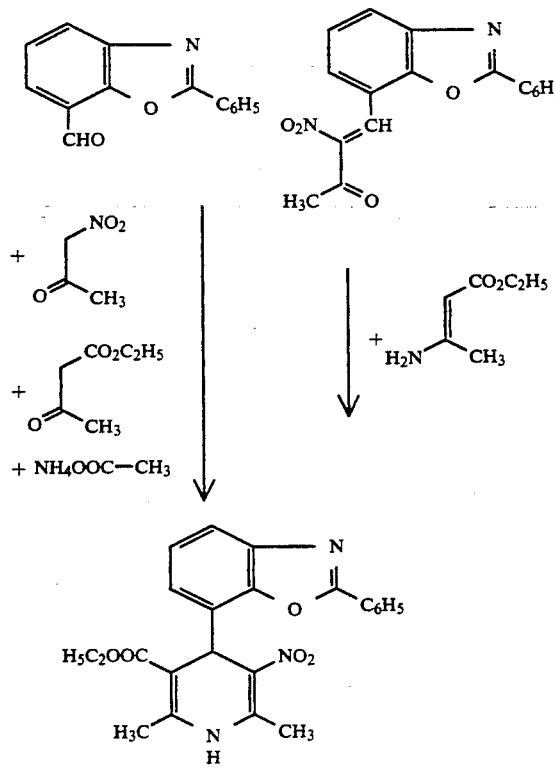

[D]

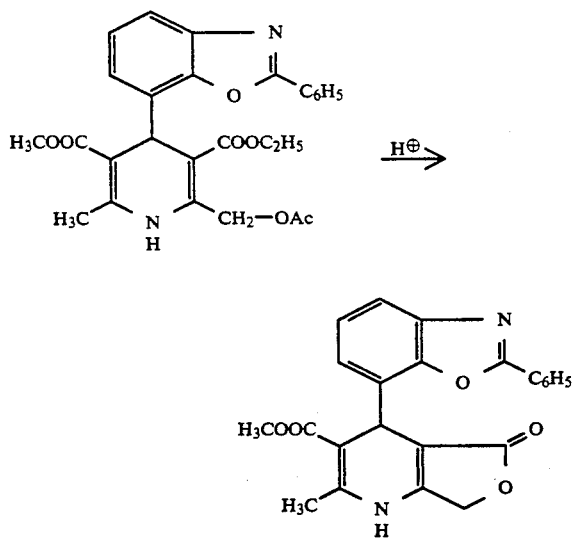

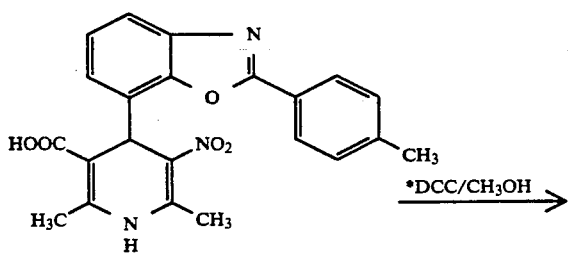

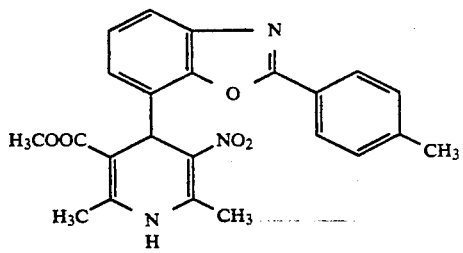

\* = dicyclohexylcarbodiimide

Suitable solvents for processes [A], [B] and [C] are all inert organic solvents. These preferably include alcohols such as methanol, ethanol, n- or iso-propanol, ethers such as diethyl ether, tetrahydrofuran, dioxane or glycol monoethyl ether or glycol diethyl ether, glacial acetic acid, pyridine, dimethylformamide, dimethyl sulphoxide, acetonitrile or hexamethylphosphoric triamide or toluene.

Suitable solvents for process [D] are the abovementioned solvents with the exception of the alcohols.

The reaction temperature for the processes [A], [B], [C] and [D] can be varied within a relatively wide range. In general, the reaction is carried out in a range from 10° C. to 200° C., preferably from 20° C. to 150° C.

The processes can be carried out at normal pressure, and at elevated or reduced pressure (for example from 0.5 to 5 bar), preferably at normal pressure.

When carrying out the processes according to the invention, any desired ratio of the substances participating in the reaction can be used. In general, however, molar amounts of the reactants are used.

Suitable reagents for the activation of the carboxylic acid are the customary reagents such as inorganic halides, for example thionyl chloride, phosphorus trichloride or phosphorus pentachloride, or carbonyldiimidazole, carbodiimides such as dicyclohexylcarbodiimide or 1-cyclohexyl-3-[2-(N-methylmorpholino)ethyl]-carbodiimide-p-toluenesulphonate or N-hydroxyphthalimide or N-hydroxy-benzotriazole.

Enantiomerically pure forms are obtained, for example, by separating mixtures of diastereomers of the compounds of the general formula (I), in which $R^4$ represents an optical ester radical, by a customary method, then preparing the enantiomerically pure carboxylic acids and then, if desired, converting them into the enantiomerically pure dihydropyridines by esterification with appropriate alcohols.

Chiral ester radicals which are suitable are all esters of enantiomerically pure alcohols such as, for example, 2-butanol, 1-phenylethanol, lactic acid, lactic acid esters, mandelic acid, mandelic acid esters, 2-aminoalcohols, sugar derivatives and many other enantiomerically pure alcohols.

The diastereomers are in general separated either by fractional crystallization, by column chromatography or by Craig partition. Which is the optimum process must be decided from case to case, and sometimes it is also expedient to use combinations of the individual processes. Separation by crystallization or Craig partition or a combination of both processes is particularly suitable.

The enantiomerically pure dihydropyridines are preferably esterified in ethers such as diethyl ether or tetrahydrofuran, dimethylformamide, methylene chloride, chloroform, acetonitrile or toluene.

The aldehydes of the general formula (II) are also new and can be prepared by a process in which
a) either compounds of the general formula (IX)

$$R^{3'}—CH_3 \qquad (IX)$$

in which
R$^{3'}$ represents the radicals of the formula

[structure with R$^6$, S, N, R$^7$]

or

[structure with R$^6$, N, S, R$^7$], in which
R$^6$ and R$^7$ have the abovementioned meanings,
are halogenated to give compounds of the general formula (X)

$$R^{3'}—CH_2—Hal \qquad (X)$$

in which
R$^{3'}$ has the abovementioned meaning and
Hal represents halogen, preferably bromine,
reacted with acetate ions and then hydrolyzed to give compounds of the general formula (XI)

$$R^{3'}—CH_2OH \qquad (XI)$$

in which
R$^{3'}$ has the abovementioned meaning,
and in a last step oxidized by a customary method,
b) or by a process in which compounds of the general formula (XII)

$$R^{3''}—CH_3 \qquad (XII)$$

in which
R$^{3''}$ represents a radical of the formula

[structure with R$^6$, O, N, R$^7$]

or

[structure with R$^6$, N, O, R$^7$], in which
R$^6$ and R$^7$ have the abovementioned meanings,
are halogenated to give compounds of the general formula (XIII)

$$R^{3''}—CH(Br)_2 \qquad (XIII)$$

in which
R$^{3''}$ has the abovementioned meaning,
and then hydrolyzed by a customary method.

The process according to the invention can be illustrated by way of example by the following equation:

[structure: benzene ring with S, N–C$_6$H$_5$ and CHO] $\xrightarrow{\text{NBS}}$

[structure with CH$_2$Br] $\xrightarrow{\text{CH}_3\text{COO}^\ominus}$

[structure with CH$_2$—OAc] $\xrightarrow{\text{OH}^\ominus/\text{H}_2\text{O}}$

[structure with CH$_2$OH] $\xrightarrow{\text{Ox}}$

[structure with CHO]

[structure with O, N–C$_6$H$_5$ and CHBr$_2$] $\xrightarrow{\text{H}_2\text{O}/\text{H}^\oplus}$

[structure with CHO]

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoric triamide or dimethylformamide, or acetic acid. It is also possible to use mixtures of the solvents mentioned.

Suitable oxidizing agents in the case of the hydroxymethyl compounds are, for example, manganese dioxide, dimethyl sulphoxide, ceric ammonium nitrate, dipyridine-chromium(VI) oxide, sodium dichromate, iodosobenzene, pyridine chlorochromate, silver carbonate on celite or Jones reagent. Manganese dioxide is preferred.

The oxidations and reductions can be carried out at normal pressure or at elevated or reduced pressure (for example from 0.5 to 5 bar), preferably at normal pressure.

The compounds of the general formula (IX) are known [compare Acta Chem. Second Ser B., 31, 203 (1977)].

The compounds of the general formula (X) are known or can be prepared by methods known from the literature [compare J. Org. Chem. 46, 3259 (1981)].

The acetoacetic esters of the formula (III) are known or can be prepared by customary methods [compare D. Borrmann, "Umsetzung von Diketonen mit Alkoholen, Phenolen und Mercaptanen" (Reaction of diketones with alcohols, phenols and mercaptans), in Houben-Weyl, Methoden der organischen Chemie, (Methods of Organic Chemistry), Vol. VIII/4, 230 et seq. (1968)].

The ylidene compounds (IV) and (VII) are new, but can be prepared by customary methods [compare H. Dornow and W. Sassenberg, Liebigs Ann. Chem. 602, 14 (1957)].

The aminocrotonic acid derivatives of the formula (VI) and (VIII) are known or can be prepared by known methods [S. A. Glickman, A. C. Cope, J. Am. Chem. Soc. 67, 1017 (1946)].

The compounds of the general formula (V) are also known [compare N. Levy, C. W. Scaife, J. Chem. Soc. (London) 1946, 1100; C. D. Hurd, M. E. Nilson, J. Org. Chem. 20, 927 (1955)].

The above preparation processes are only indicated for clarification. The preparation of the compounds of the formula (I) and (II) is not restricted to these processes, but any modification of these processes can be used in the same way for the preparation of the compounds according to the invention.

The compounds according to the invention exhibit an unforeseeable, valuable pharmacological action spectrum. They influence the contractility of the heart and the tone of the smooth musculature. They can therefore be employed in medicaments for influencing pathologically altered blood pressure, as coronary therapeutics and for the treatment of cardiac insufficiency. Moreover, they can be used for the treatment of cardiac arrhythmias, for the reduction of blood sugar, for the detumescence of mucosal membranes and for influencing the salt and fluid balance.

The cardiac and vascular effects were discovered in the isolated perfused guinea-pig heart.

For this, the hearts of 250 to 350 g guinea-pigs are used. The animals are sacrificed by a blow to the head, the thorax is opened and a metal cannula is tied into the exposed aorta. The heart is separated out of the thorax with the lungs and attached to the perfusion apparatus with continuous perfusion via an aortic cannula. The lungs are separated at the lung roots. A KrebsHenseleit solution (1) (118.5 mmol/l of NaCl, 4.75 mmol/l of KCl, 1.19 mmol/l of KH$_2$PO$_4$, 1.19 mmol/l of MgSO$_4$, 25 mmol/l of NaHCO$_3$, 0.013 mmol/l of Na$_2$EDTA) whose CaCl$_2$ content is 1.2 mmol/l is used as the perfusion medium. 10 mmol/l of glucose are added as an energy-producing substrate. The solution is filtered particle-free before the perfusion. The solution is aerated with carbogen (95% O$_2$, 5% CO$_2$) to maintain a pH of 7.4. The hearts are perfused with a constant flow (10 ml/min) at 32° C. by means of a peristaltic pump.

To measure the cardiac function, a liquid-filled latex balloon which is connected to a pressure transducer via a liquid column is inserted through the left auricle into the left ventricle, and the isovolumetric contractions are recorded on a rapid recorder (Opie, L., J. Physiol 180 (1965), 529–541). The perfusion pressure is recorded by means of a pressure transducer which is connected to the perfusion system upstream of the heart. Under these conditions, a reduction in the perfusion pressure indicates a coronary dilatation, and an increase or decrease in the left ventricular contraction amplitude indicates a reduction or an increase in the heart contractility. The compounds according to the invention are perfused into the perfusion system in suitable dilutions shortly upstream of the isolated heart.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In general it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to deviate from the amounts mentioned, in particular depending on the body weight or the type of administration route, on individual behaviour towards the medicament, the nature of its formulation and the point in time or interval at which administration takes place. Thus, in some cases it may be sufficient to manage with less than the above-mentioned minimum amount, while in other cases the upper limit mentioned must be exceeded. In the case of the administration of larger amounts, it may be advisable to divide these into several individual doses over the course of the day.

PREPARATION OF THE STARTING COMPOUNDS

Example I

4-Bromomethyl-2-phenyl-benzothiazole

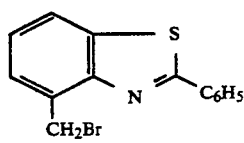

42.8 g (190 mmol) of 4-methyl-2-phenyl-benzothiazole [compare Perregaard, Lawesson, Acta Chem.

Scand. Ser. B, 31, 203 (1977)] were dissolved in 1 l of carbon tetrachloride, and catalytic amounts of 2,2'-azoisobutyronitrile were added. 40.6 g (0.228 mol) of N-bromosuccinimide (NBS) were were added under reflux in portions and the mixture was boiled overnight. A further 40.6 g of NBS were added and the mixture was boiled for 2 h. After cooling, the mixture was diluted with methylene chloride, washed with water, dried and concentrated, and the residue was crystallized using petroleum ether.

Yield: 53 g (92% of theory)
M.p.: 114°–115° C.

Example II

4-Acetoxymethyl-2-phenyl-benzothiazole

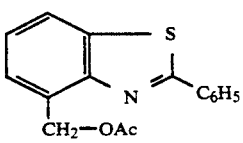

53 g (0 176 mol) of the compound from Example I and 20 g (0.2 mol) of potassium acetate were stirred at room temperature in 500 ml of dimethylformamide for 24 h, the solvent was stripped off in vacuo, water was added, and the product was filtered off with suction and dried.

Yield: 46 g (92% of theory)
M.p.: 83°–84° C.

Example III

4-Hydroxymethyl-2-phenyl-benzothiazole

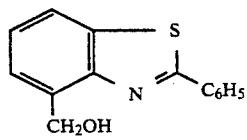

43 g of the compound from Example II were dissolved in 1 l of absolute methanol, 5 g of potassium carbonate were added and after 10 minutes at room temperature the mixture was concentrated. The residue was taken up using methylene chloride, and the solution was washed, dried and concentrated. 90% of theory of the title compound was obtained.

M.p.: 116°–117° C.

Example IV

2-Phenyl-benzothiazole-4-carbaldehyde

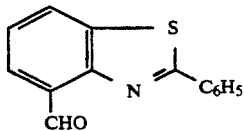

26.5 g (0.11 mol) of the compound from Example III were dissolved in 400 ml of methylene chloride and the mixture was boiled under reflux with 50 g of manganese dioxide (active) overnight. After cooling, the solid was filtered off with suction and the filtrate was concentrated.

Yield: 25 g (85% of theory)

M.p.: 127°–128° C.

Example V

2'-Chloro-3'-methyl-benzanilide

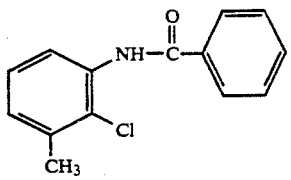

57 g (0.4 mol) of 2-chloro-3-methyl-aniline [CA 89, 30772h) were dissolved in 1.5 l of toluene, 55 g of potassium carbonate were added and 62 g (0.4 mol) of benzoyl chloride were added dropwise at 80° C. After reaction is complete, the solid was filtered off in the cold and washed with water, and the filtrate was dried. After concentrating and triturating with petroleum ether 98 g of product (100%) crystallized.

M.p.: 125°–126° C.

Example VI

2'-Chloro-3'-methyl-thiobenzanilide

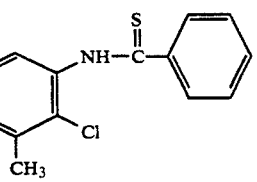

98 g (0.4 mol) of the compound from Example V and 162 g (0.4 mol) of Lawesson's reagent were boiled in 1 l of toluene overnight, and the mixture was concentrated and purified on SiO$_2$(cyclohexane/ethyl acetate=8:2)

Yield: 93 g (80% of theory) as a yellow oil.

Example VII

7-Methyl-2-phenyl-benzothiazole

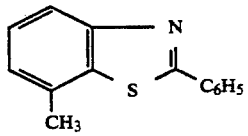

91.6 g (0.35 mol) of the compound from Example VI in 1 l of dimethylformamide were boiled under reflux with 64 g (0.42 mol) of diazabicycloundecane for 3 h. The mixture was concentrated, the residue was taken up in methylene chloride/water, and the solution was rendered weakly acidic, washed with water, dried and concentrated.

Yield: 70 g (89% of theory)
M.p.: 53°–54° C.

Example VIII

7-Bromomethyl-2-phenyl-benzothiazole

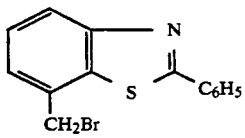

The compound was obtained in analogy to Example I.

M.p.: 104°–105° C.

Example IX

7-Acetoxymethyl-2-phenyl-benzothiazole

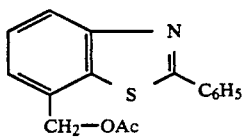

The compound was obtained in analogy to the procedure for Example II.

M.p.: 64°–65° C.

Example X

7-Hydroxymethyl-2-phenyl-benzothiazole

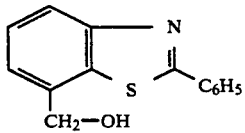

The compound was obtained in analogy to the procedure for Example III.

M.p.: 86°–87° C.

Example XI

2-Phenyl-benzothiazole-7-carbaldehyde

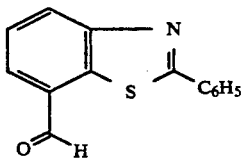

The compound was obtained in analogy to the procedure for Example IV.

M.p. 136° C.

Example XII

4-Dibromomethyl-2-phenyl-benzoxazole

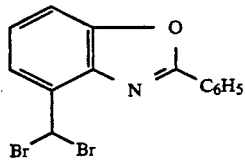

3.5 g (17 mmol) of 4-methyl-2-phenyl-benzoxazole [J. Org. Chem. 46, 3259 (1981)] and 6 g of N-bromosuccinimide in 150 ml of carbon tetrachloride were boiled under reflux with catalytic amounts of 2,2'-azoisobutyronitrile. After 7 hours, a further 6 g of N-bromosuccinimide and 2,2'-azoisobutyronitrile were added and the mixture was boiled for a further 7h. After cooling, it was washed with water, dried and concentrated.

Yield: 5.9 g (96% of theory)

M.p.: 106° C.

Example XIII

2-Phenylbenzoxazole-4-carbaldehyde

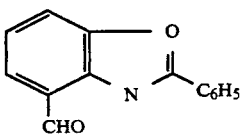

5.5 g (14.9 mmol) of the compound from Example XII were stirred at 100° C. with 30 ml of concentrated sulphuric acid for 1 h, the mixture was poured into water, and the precipitate was filtered off with suction and dried.

Yield: 3.3 g (100% of theory)

M.p. 116° C.

Example XIV

Methyl 3-benzoylamino-2-hydroxy-benzoate

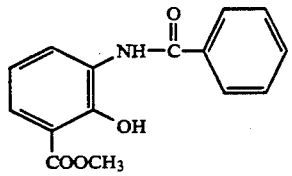

20 mmol of methyl 3-amino-2-hydroxy-benzoate were stirred at room temperature in toluene with 20 mmol of benzoyl chloride for 4 hours with the addition of dimethylaniline, the mixture was concentrated and the residue was recrystallized from EtOH. M.p.: 105° C.

Example XV

Methyl 2-benzoxazole-7-carboxylate

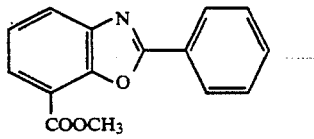

5.8 ml of CCl$_4$ in 5 ml of acetonitrile were added to 30 mmol of the compound from Example XIV, 30 mmol of benzoic acid, 50 mmol of triphenylphosphine and 120 mmol of triethylamine in 100 ml of acetonitrile at 3° C. under argon in the course of 15 min and the mixture was stirred at room temperature for 20 hours and concentrated, diethyl ether was added to the residue, the solid was filtered off with suction, the filtrate was concentrated and the residue was separated on silica gel. M.p.: 77° C. (white needles)

Example XVI

7-Hydroxymethyl-2-phenyl-benzoxazole

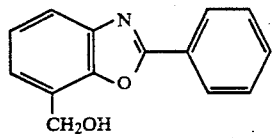

10 mmol of the compound from Example XV were dissolved in 50 ml of toluene, then 40 ml of DI-BAH*(20% strength in toluene) were added at 0° C. and the mixture was stirred at room temperature for 2 h. After working up with sulphuric acid, the title compound was obtained.

*=diisobutylaluminiumhydrid

M.p.: 131° C. (from ether)

Example XVII

2-Phenyl-benzoxazole-7-carbaldehyde

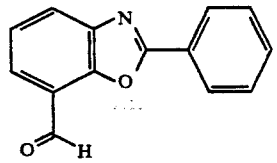

10 mmol of the compound from Example XVI were boiled under reflux with 50 mmol of MnO$_2$(active) in 50 ml of acetone for 6 h, the solid was filtered off with suction and the filtrate was concentrated. The residue was recrystallized from isopropanol. M.p.: 107° C.

Example XVIII 2-(3-Pyridyl)-benzoxazole-7-carbaldehyde

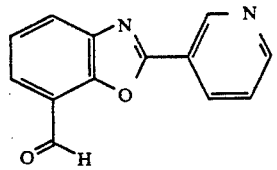

The compound was prepared analogously to the procedures of Examples XIV to XVII.
M.p.: 140° C. (yellow needles).

PREPARATION EXAMPLES

Example 1

Isopropyl 3-cyano-2,6-dimethyl-4-(2-phenyl-benzothiazol-7-yl)-1,4-dihydropyridine-5-carboxylate

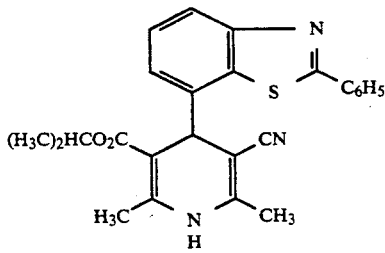

10 mmol of 2-phenyl-benzothiazole-7-carboxaldehyde, 10 mmol of isopropyl acetoacetate and 10 mmol of 3-aminocrotononitrile are boiled overnight in 20 ml of ethanol, the mixture is concentrated and the residue is purified on a silica gel column (cyclohexane/ethyl acetate=6:4)

Yield: 28% of theory
M.p.: 218° C.

The compounds shown in Tables 1, 2 and 3 were prepared in analogy to the procedure of Example 1:

TABLE 1

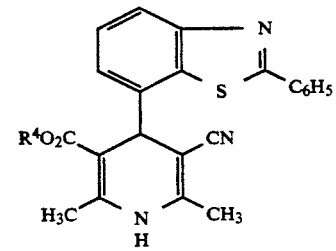

| Example No. | R$^4$ | M.p. (°C.) |
|---|---|---|
| 2 | —C$_2$H$_5$ | 249 |
| 3 | —CH$_3$ | 240–241 |
| 4 | —CH(CH$_3$)—CO$_2$C$_2$H$_5$ | 178 |
| 5 | —CH(CH$_3$)—CO$_2$H | amorphous |

TABLE 2

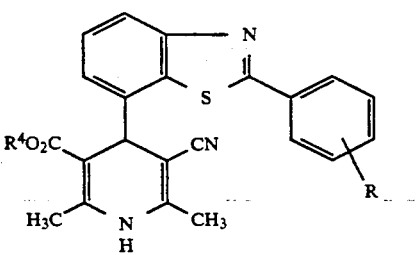

| Example No. | R⁴ | R | M.p. (°C.) |
|---|---|---|---|
| 6 | —CH₃ | H | 218 |
| 7 | —C₂H₅ | H | 236 |
| 8 | —CH(CH₃)₂ | H | 198 |
| 9 | —C₂H₅ | 2-Cl | 241 |
| 10 | —C₂H₅ | 3-F | 222 |
| 11 | —C₂H₅ | 4-F | 254 |
| 12 | —C₂H₅ | 2-F | 216 |
| 13 | —C₂H₅ | 3-Cl | 232 |
| 14 | —C₂H₅ | 4-Cl | 212 |

TABLE 3

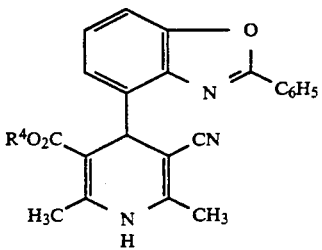

| Example No. | R⁴ | M.p. (°C.) |
|---|---|---|
| 15 | —C₂H₅ | 246 |

Example 16

Methyl 2,6-dimethyl-3-nitro-4-(2-phenyl-benzothiazol-7-yl)-1,4-dihydropyridine-5-carboxylate

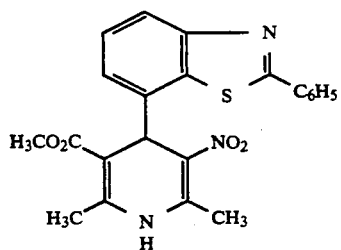

10 mmol of 2-phenyl-benzothiazole-7-carboxaldehyde, 10 mmol of nitroacetone and 10 mmol of methyl 3-aminocrotonate are boiled in 20 ml of ethanol overnight, the mixture is concentrated and the residue is purified on a silica gel column (cyclohexane/ethyl acetate=6:4)

Yield: 25% of yellow crystals
M.p. 233° C. (dec.)

The compounds shown in Tables 4, 5 and 6 were prepared in analogy to the procedure of Example 16:

TABLE 4

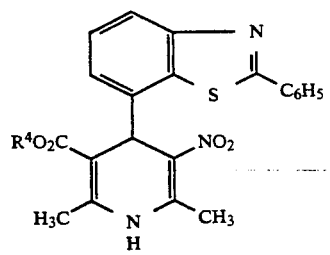

| Example No. | R⁴ | M.p. (°C.) |
|---|---|---|
| 17 | —C₂H₅ | 222 |
| 18 | —CH(CH₃)₂ | 215 |

TABLE 5

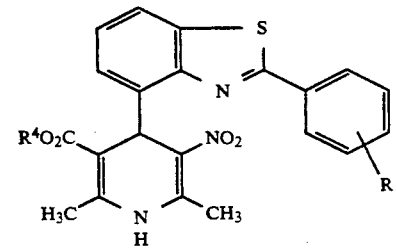

| Example No. | R⁴ | R | M.p. (°C.) |
|---|---|---|---|
| 19 | —C₂H₅ | H | 234 |
| 20 | —C₂H₅ | 2-Cl | 196 |
| 21 | —C₂H₅ | 3-F | 204 |
| 22 | —C₂H₅ | 4-F | 238 |
| 23 | —C₂H₅ | 2-F | 221 |
| 24 | —C₂H₅ | 3-Cl | 221 |
| 25 | —C₂H₅ | 4-Cl | 246 |

TABLE 6

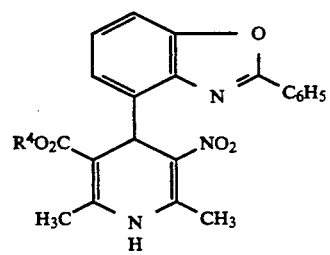

| Example No. | R⁴ | M.p. (°C.) |
|---|---|---|
| 26 | —C₂H₅ | 229 |

Example 27

Methyl 2-methyl-5-oxo-4-(2-phenyl-benzothiazol-7-yl)-1,4,5,7-tetrahydrofuro[3,4-b]pyridine-3-carboxylate

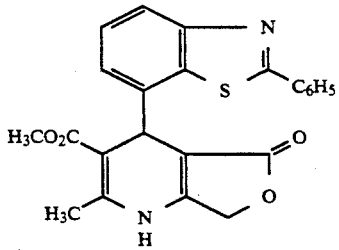

10 mmol of 2-phenyl-benzothiazole-7-carboxaldehyde, 10 mmol of 4-acetoxyacetoacetic ester and 10 mmol of methyl 3-aminocrotonate are boiled in 20 ml of methanol overnight, then 6 ml of dilute hydrochloric acid are added and the mixture is boiled for 30 minutes. It is concentrated and purified on a silica gel column (cyclohexane/ethyl acetate=1:1).

Yield: 30%
M.p.: 275° C.

The compounds shown in Tables 7 and 8 were prepared in analogy to the procedure of Example 27:

TABLE 7

| Example No. | $R^4$ | M.p. (°C.) |
|---|---|---|
| 28 | —$C_2H_5$ | 165 |
| 29 | —$CH(CH_3)_2$ | 195 |

TABLE 8

| Example No. | $R^4$ | R | M.p. (°C.) |
|---|---|---|---|
| 30 | —$CH_3$ | H | 285 |
| 31 | —$C_2H_5$ | H | 249 |
| 32 | —$CH(CH_3)_2$ | H | 210 |
| 33 | —$C_2H_5$ | 2-Cl | 168 |
| 34 | —$C_2H_5$ | 3-F | 267 |
| 35 | —$C_2H_5$ | 4-F | 199 |
| 36 | —$C_2H_5$ | 2-F | 196 |
| 37 | —$C_2H_5$ | 3-Cl | 234 |
| 38 | —$C_2H_5$ | 4-Cl | 198 |

The compounds shown in Table 9 were prepared in analogy to the procedure of Example 1.

TABLE 9

| Example No. | $R^4$ | M.p. (°C.) |
|---|---|---|
| 39 | —$CH(CH_3)_2$ | 191 |
| 40 | —$CH_3$ | 199 |

The compounds shown in Table 10 were prepared in analogy to the procedure of Example 16.

TABLE 10

| Example No. | $R^4$ | M.p. (°C.) |
|---|---|---|
| 41 | —$C_2H_5$ | 246 |
| 42 | —$CH_3$ | 245 |

The compounds shown in Table 11 were prepared in analogy to the procedure of Example 17.

TABLE 10

| Example No. | $R^4$ | M.p. (°C.) |
|---|---|---|
| 43 | —$C_2H_5$ | 160 |

It will be understood that the specificatin and examples are illustrative but not limitative of the present invention and that other embodimetns within the spirit and scope of the invention will suggest themselves to those skilled in the art.

We claim:

1. A 4-hetero-substituted-1,4-dihydropyridine of the formula

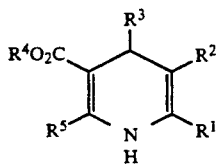 (I)

in which
R¹ and R⁵ are identical or different and represent straight-chain or branched alkyl having up to 8 carbon atoms,
R² represents nitro or cyano,
R³ represents a radical of the formula

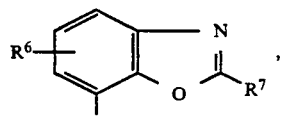

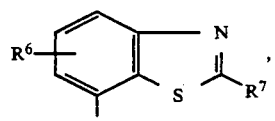

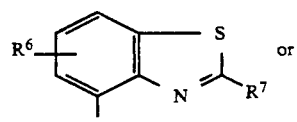 or

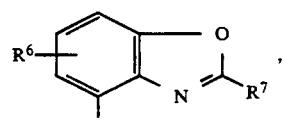, in which
R⁶ denotes hydrogen, halogen or straight-chain or branched alkyl or alkoxy in each case having up to 8 carbon atoms,
R⁷ denotes aryl having 6 to 10 carbon atoms, which is optionally monosubstituted or disubstituted by identical or different substituents from the group consisting of halogen, nitro, cyano, trifluoromethyl, trifluoromethoxy, trifluoromethylthio, straight-chain or branched alkyl, alkoxy or alkoxycarbonyl in each case having up to 8 carbon atoms, and carboxyl, or
denotes thienyl or pyridyl,
R⁴ represents hydrogen, or
represents straight-chain or branched alkyl, alkenyl, alkadienyl or alkynyl in each case having up to 10 carbon atoms which are optionally monosubstituted or disubstituted by identical or different substituents from the group consisting of halogen, hydroxyl, carboxyl, cyano, nitro, phenoxy and straight-chain or branched alkylthio, alkoxy, alkoxycarbonyl, acyl or acyloxy in each case having up to 8 carbon atoms, and phenoxy or phenyl optionally monosubstituted or disubstituted by identical or different substituents from the group consisting of halogen and straight-chain or branched alkyl or alkoxy in each case having up to 6 carbon atoms,
or a physiologically acceptable salt thereof.

2. A compound or salt thereof according to claim 1, in which
R¹ and R⁵ are identical or different and represent straight-chain or branched alkyl having up to 6 carbon atoms,
R² represents nitro or cyano,
R³ represents a radical of the formula

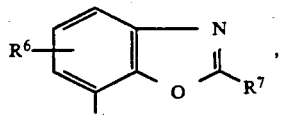,

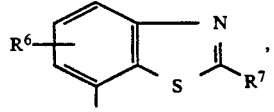,

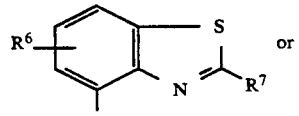 or

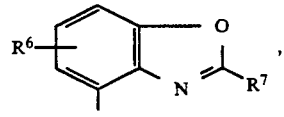, in which
R⁶ denotes hydrogen, fluorine, chlorine or straight-chain or branched alkyl or alkoxy in each case having up to 2 carbon atoms,
R⁷ denotes phenyl which is optionally substituted by fluorine, chlorine, nitro, cyano, trifluoromethyl or by straight-chain or branched alkyl or alkoxy in each case having up to 6 carbon atoms, or
denotes pyridyl or thienyl,
R⁴ represents hydrogen or
represents straight-chain or branched alkyl or alkenyl in each case having up to 8 carbon atoms which are optionally substituted by fluorine, chlorine, hydroxyl, carboxyl, cyano, nitro or by straight-chain or branched alkylthio, alkoxy, alkoxycarbonyl, acyl or acyloxy in each case having up to 6 carbon atoms or by phenoxy or phenyl.

3. A compound or salt thereof according to claim 1 in which
R¹ and R⁵ are identical or different and represent straight-chain or branched alkyl having up to 4 carbon atoms,
R² represents nitro or cyano,
R³ represents a radical of the formula

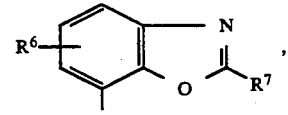,

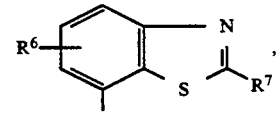,

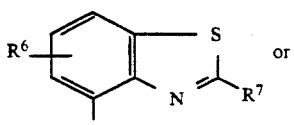

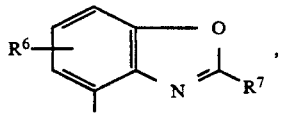

in which

R⁶ denotes hydrogen, chlorine or methyl,

R⁷ denotes phenyl which is optionally substituted by fluorine, chlorine, nitro, trifluoromethyl or by straight-chain or branched alkyl, acyl or alkoxy in each case having up to 4 carbon atoms, or denotes pyridyl, R⁴ represents hydrogen, or
represents straight-chain or branched alkyl having up to 6 carbon atoms, which is optionally substituted by hydroxyl, carboxyl, cyano or by straight-chain or branched alkoxycarbonyl, alkoxy or acyloxy in each case having up to 4 carbon atoms.

4. A compound according to claim 1, wherein such compound is ethyl 3-cyano-2,6-dimethyl-4-(2-phenyl-benzothiazol-4-yl)-1,4-dihydropyridine-5-carboxylate of the formula

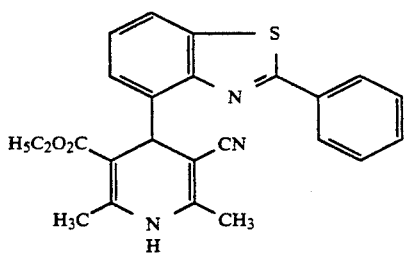

or a physiologically acceptable salt thereof.

5. A compound according to claim 1, wherein such compound is isopropyl 3-cyano-2,6-dimethyl-4-(2-phenyl-benzothiazol-4-yl)-1,4-dihydropyridine-5-carboxylate of the formula

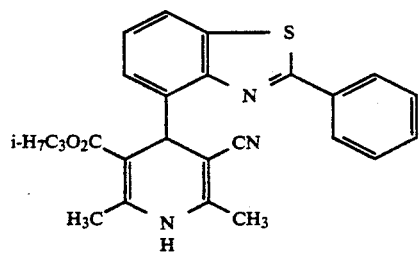

or a physiologically acceptable salt thereof.

6. A compound according to claim 1, wherein such compound is ethyl 3-cyano-2,6-dimethyl-4-[2-(3-fluorophenyl)-benzothiazol-4-yl]-1,4-dihydropyridine-5-carboxylate of the formula

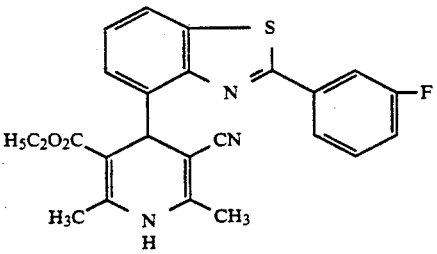

or a physiologically acceptable salt thereof.

7. A compound according to claim 1, wherein such compound is ethyl 3-cyano-2,6-dimethyl-4-[2-(4-fluorophenyl)-benzothiazol-4-yl]-1,4-dihydropyridine-5-carboxylate of the formula

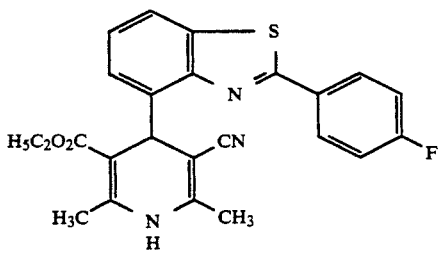

or a physiologically acceptable salt thereof.

8. A compound according to claim wherein such compound is ethyl 3-cyano-2,6-dimethyl-4-[2-(2-fluorophenyl)-benzothiazol-7-yl]-1,4-dihydropyridine-5-carboxylate of the formula

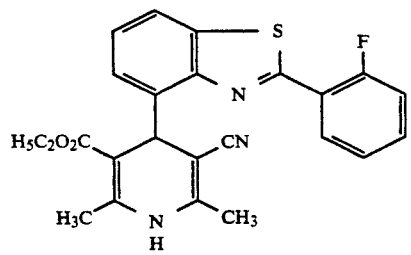

or a physiologically acceptable salt thereof.

9. A composition exhibiting positive inotropic action comprising an amount effective therefore of a compound or salt according to claim 1 and a physiologically acceptable diluent.

10. In the method of treating a patient for coronary vessel disorders by administration of an effective amount of a compound which exhibits positive inotropic activity, the improvement wherein said compound is a compound or salt thereof according to claim 1.

11. The method according to claim 10, wherein such compound is
ethyl 3-cyano-2,6-dimethyl-4-(2-phenyl-benzothiazol-4-yl)-1,4-dihydropyridine-5-carboxylate,
isopropyl 3-cyano-2,6-dimethyl-4-(2-phenylbenzothiazol-4-yl)-1,4-dihydropyridine-5-carboxylate,
ethyl 3-cyano-2,6-dimethyl-4-[2-(3-fluorophenyl)-benzothiazol-4yl]-1,4-dihydropyridine-5-carboxylate,
ethyl 3-cyano-2,6-dimethyl-4-[2-(4-fluorophenyl)-benzothiazol-4-yl]-1,4-dihydropyridine-5-carboxylate or
ethyl 3-cyano-2,6-dimethyl-4-[2-(2-fluorophenyl)-benzothiazol-4-yl]-1,4-dihydropyridine-5-carboxylate, or a physiologically acceptable salt thereof.

* * * * *

UNITED STATES PATENT AND TRADEMARK OFFICE
CERTIFICATE OF CORRECTION

PATENT NO. : 5,200,420
DATED : April 6, 1993
INVENTOR(S) : Goldmann et al.

It is certified that error appears in the above-identified patent and that said Letters Patent is hereby corrected as shown below:

| | |
|---|---|
| Title Page & Col. 1 line 2 | Invention [54]: After " -YL " insert -- ) -- |
| Title Page | U.S. PATENT DOCUMENTS: After " 4,380,547 " delete " 7/1983 " and substitute -- 4/1983-- |
| Col. 26, line 30 | After " claim " insert -- 1 -- |
| Col. 26, line 32 | Delete " 7 " and substitute -- 4 -- |

Signed and Sealed this

Sixteenth Day of August, 1994

Attest:

BRUCE LEHMAN

*Attesting Officer*  *Commissioner of Patents and Trademarks*